United States Patent [19]

Carney et al.

[11] Patent Number: 5,324,391

[45] Date of Patent: Jun. 28, 1994

[54] METHOD FOR CROSSLINKING CELLULOSE FIBERS

[75] Inventors: Allan R. Carney, Puyallup; Peter A. Graef, Tacoma; Mark W. Bowns, Auburn; Clifford R. Bolstad, Milton; Fred E. Olmstead, Federal Way, all of Wash.

[73] Assignee: Weyerhaeuser Company, Tacoma, Wash.

[21] Appl. No.: 974,365

[22] Filed: Nov. 9, 1992

Related U.S. Application Data

[63] Continuation of Ser. No. 607,268, Oct. 31, 1990, abandoned.

[51] Int. Cl.$^5$ .......................................... D21H 17/05
[52] U.S. Cl. ...................................... 162/9; 162/100; 162/157.6; 162/182; 162/201
[58] Field of Search ................ 162/9, 100, 157.6, 182, 162/201

[56] References Cited

U.S. PATENT DOCUMENTS

| | | | |
|---|---|---|---|
| 2,236,969 | 4/1941 | Flateboe | 83/6 |
| 2,894,697 | 7/1959 | Panning et al. | 241/154 |
| 3,208,626 | 9/1965 | Jensen | 241/195 |
| 3,395,708 | 8/1968 | Hervey et al. | 128/284 |
| 3,440,135 | 4/1969 | Chung | 162/157 |
| 3,482,788 | 12/1969 | Newell | 241/69 |
| 3,519,211 | 7/1970 | Sakulich et al. | 241/18 |
| 3,554,862 | 1/1971 | Hervey et al. | 162/158 |
| 3,637,146 | 1/1972 | Banks | 241/194 |
| 3,658,613 | 4/1972 | Steiger | 156/153 |
| 3,677,886 | 7/1972 | Forssbald et al. | 162/72 |
| 3,750,962 | 8/1973 | Morgan, Jr. | 241/18 |
| 3,765,971 | 10/1973 | Fleissner | 156/62.2 |
| 3,819,470 | 6/1974 | Shaw et al. | 162/157 |
| 3,825,194 | 7/1974 | Buell | 241/191 |
| 3,901,236 | 8/1975 | Assarsson et al. | 128/284 |
| 3,950,218 | 4/1976 | Levesque | 162/201 |
| 3,950,219 | 4/1976 | Levesque | 162/201 |
| 3,966,126 | 6/1976 | Werner | 241/18 |
| 3,987,968 | 10/1976 | Moore et al. | 241/28 |
| 4,144,122 | 3/1979 | Emanuelsson et al. | 162/158 |
| 4,241,881 | 12/1980 | Laumer | 241/28 |
| 4,252,279 | 2/1981 | Johansson et al. | 241/27 |

(List continued on next page.)

FOREIGN PATENT DOCUMENTS

| | | |
|---|---|---|
| 806352 | 2/1969 | Canada . |
| 0190634 | 8/1986 | European Pat. Off. . |
| 0225940 | 6/1987 | European Pat. Off. . |
| 0399564 | 5/1990 | European Pat. Off. . |
| 0427316A2 | 5/1991 | European Pat. Off. . |
| 0427317A2 | 5/1991 | European Pat. Off. . |
| 0429112A2 | 5/1991 | European Pat. Off. . |
| 0440472A1 | 8/1991 | European Pat. Off. . |
| 2902257 | 7/1980 | Fed. Rep. of Germany . |
| 159148 | 2/1983 | German Democratic Rep. . |
| 93769 | 4/1959 | Norway . |
| WO84/00904 | 3/1984 | PCT Int'l Appl. . |
| 850432 | 8/1982 | U.S.S.R. . |
| 437242 | 10/1935 | United Kingdom . |
| 680266 | 10/1952 | United Kingdom . |
| 1183457 | 3/1970 | United Kingdom . |

*Primary Examiner*—Peter Chin
*Attorney, Agent, or Firm*—Klarquist Sparkman Campbell Leigh & Whinston

[57] ABSTRACT

A method is disclosed for preparing a quantity of individual treated fibers from one or more fiber mats in a treatment apparatus. The apparatus comprises a fiber treatment zone, a conveyor for conveying each mat through the fiber treatment zone, wherein each mat is impregnated by an applicator with a crosslinking substance, and directly to an attrition device. The attrition device fiberizes the mats to form a fiber output having a low nit level, such as no more than about three, and a dryer for both drying the fiber output and curing the crosslinking substance. The fiberizer is configured to have minimize the accumulation of fiber at locations therein. An optional component of the fiberizer is a novel fluff generator comprised of multiple rotors each having plural longitudinally extended rows of radially extending rotor pins that rotate past groups of shorter pins mounted on the inside surface of the fluff generator housing.

8 Claims, 8 Drawing Sheets

U.S. PATENT DOCUMENTS

| | | | |
|---|---|---|---|
| 4,303,471 | 12/1981 | Laursen | 162/158 |
| 4,351,699 | 9/1982 | Osborn, III | 162/112 |
| 4,406,415 | 9/1983 | Greer | 241/194 |
| 4,476,323 | 10/1984 | Hellsten et al. | 564/294 |
| 4,533,507 | 8/1985 | Tao | 261/153 |
| 4,572,440 | 2/1986 | Tao | 241/23 |
| 4,600,462 | 7/1986 | Watt | 156/278 |
| 4,650,127 | 3/1987 | Radwanski et al. | 241/28 |
| 4,729,516 | 3/1988 | Williams, Jr. | 241/189 R X |
| 4,822,453 | 4/1989 | Dean et al. | 162/157 |
| 4,853,086 | 8/1989 | Graef | 162/157 |
| 4,889,595 | 12/1989 | Herron et al. | 162/157 |
| 4,935,022 | 6/1990 | Lash et al. | 604/368 |

5,324,391

METHOD FOR CROSSLINKING CELLULOSE FIBERS

This application is a continuation of application Ser. No. 07/607,268, filed on Oct. 31, 1990 abandoned.

FIELD OF THE INVENTION

This invention relates to a fiber treatment apparatus and more particularly to the apparatus of the type which utilizes sprayers or other applicators to treat a fiber mat and mechanisms for subsequently fiberizing the mat following such treatment.

BACKGROUND OF THE INVENTION

Various devices are known in the art for treating fibers in mat form and thereafter breaking the mats into individual fibers. For example, reference is made to U.S. Pat. No. 3,440,135 to Chung which discloses a mechanism for applying a crosslinking agent to a cellulosic fiber mat, the passage of the mat while still wet and following "aging" through a fiberizer, such as a hammermill, etc. (without disclosing any specific details of such a fiberizer) to fiberize the mat, and drying the resulting loose fibers in a two stage dryer. The first dryer stage is at a temperature sufficient to flash water vapor from the fibers and the second dryer stage is at a temperature to effect curing of the crosslinking agent. A cyclone separator is then illustrated separating the fibers from the gas and for subsequent collection. Chung mentions the need for the "aging" step, of many hours duration, in order to reduce the level of nits in the resulting fiber product. As described below, nits are typically interbonded fibers which can interfere with product quality. Therefore, the Chung apparatus suffers from the drawback of requiring the inconvenient and costly storage of wet fiber mats (e.g. in roll form) for a substantial period of time in order to minimize nit formation.

Unfortunately, fiberization processes known in the art which employ currently available fiberizing or comminution machinery yield crosslinked fibers that have too many nits and knots to be acceptable for many uses. A probable reason is that such machinery has excess dead space where fibers are excessively pressed together and/or has localized regions of elevated temperature hot enough to cause premature curing of the crosslinking agent while fibers are in intimate contact with each other. Since fiberization is performed on a mat that is still wet with the uncured crosslinking agent, dead spaces and hot spots in the fiberizer would encourage the formation of interfiber bonds, which form nits, that virtually cannot be broken by downstream equipment.

Interfiber bonding in a conventional fiberizer apparatus can also lead to production of excessive amounts of "fines", which are undesirably short fibers due principally to fiber breakage. Crosslinking imparts substantial brittleness to cellulose fibers, which thereby exhibit limited compliance to mechanical stresses. Nits are especially susceptible to mechanical stresses because of their density which is much greater than the density of individual fibers. Excess fiber breakage and fines not only degrade absorbency but can substantially reduce the loft and resiliency of a product made from crosslinked fibers.

Hence, there is a need for an apparatus that will produce treated fibers, such as crosslink agent treated cellulose fibers, having a nit level lower than levels obtainable with existing equipment. There is also a need for such an apparatus that will produce such fibers from a mat comprised of cellulose fibers while not causing significant breakage of individual fibers of the mat.

SUMMARY OF THE INVENTION

The apparatus of the present invention is particularly adapted for preparing a quantity of individual crosslinked cellulose fibers from one or more mats comprised of non-crosslinked cellulose fibers. The apparatus comprises: a fiber treatment zone; a means for conveying each mat through the fiber treatment zone wherein each mat is impregnated with a crosslinking substance; a means for applying the crosslinking substance to each mat in the fiber treatment zone; a means for subsequently directly conveying each mat from the fiber treatment zone without requiring aging of the mat. The fiberizer fiberizes the treated mat to form a fiber output having a low nit level, such as a nit level of no more than about three; and a dryer for both drying the fiber output and curing the crosslinking substance to form dried and cured fibers.

Representative conveyors include, but are not limited to, conveyor belts and roller mechanisms. In the fiber treatment zone, the crosslinking substance can be applied to the mat via any suitable means including, but not limited to, spraying, roller coating, and a combination of spraying and roller coating.

The fiberizer apparatus comprises at least an attrition device which produces a low nit level fiber output. The fiberizer may also optionally include a disk refiner of conventional design coupled to the attrition device and a fluff generator of novel design coupled to the disk refiner.

A preferred embodiment of the attrition device comprises a substantially cylindrical rotor rotatable about a longitudinal axis and a housing surrounding the rotor. The housing may include up to six mat feeder assemblies each capable of simultaneously urging a wet or dry treated mat into engagement with the rotating rotor. The rotor includes groups or stacks of hammers extending longitudinally and radially over the surface of the rotor, such as in an alternating fashion. In a specific arrangement, any hammer group is longitudinally and radially adjacent an empty space large enough to accept a hammer group, and any said empty space is adjacent a hammer group. Air flow may be directed within the attrition device away from the ends and toward the center of the rotor therein to minimize the possible accumulation of fibers at such end locations. Also, the attrition device may include a fluid, and preferably a liquid, flushing mechanism for use in cleaning any accumulated fiber from the attrition device. The attrition device substantially lacks internal hot spots and dead spaces, thereby inhibiting formation of nits in the fibers produced by said device as shown in cross-section in FIG. 10, the inner surface of the cylindrical housing is a smooth, closed cylinder that avoids internal hot spots and dead spaces. Also, the attrition device inhibits fiber breakage.

A preferred embodiment of the fluff generator comprises three rotors having coplanar parallel longitudinal axes each surrounded by a cylindrical housing. The rotor housings are contiguous and partially intersecting. All three rotors rotate synchronously in the same direction about their axes. Each rotor comprises multiple longitudinally extended groups of multiple radially projecting pins which, during rotation of the rotor, travel past multiple, longitudinally extended groups of multiple shorter pins projecting from the inside of the corresponding rotor housing toward the rotor axis. The fluff generator is effective for providing additional comminution, if required, of the fibers, particularly of residual knots in the comminuted fibers produced by the attrition device.

The dryer defines a drying zone for forming dried fibers and a curing zone for curing the crosslinking substance in the dried fibers, thereby forming dried and cured fibers. The drying zone preferably includes a dryer inlet, for receiving the fiber output, having a temperature of about 200° C. to about 315° C. so as to flash-evaporate residual moisture from the fiber output. The curing zone preferably includes an outlet through which dried and cured fibers are delivered from the dryer, where the temperature of the outlet is typically within a range of about 140° C. to about 180° C. for cellulose fibers or at other temperatures as required so as to prevent scorching the fibers. The drying and curing zones preferably comprise a first and a second tower in which the fibers are lofted to ensure thorough fiber separation. In the dryer, flash drying of the fibers occurs which microscopically explosively separates fibers loosely adhering together in the form of a fiber knot.

An object of the present invention is to provide an apparatus for producing treated fibers, such as crosslinked cellulose fibers, with a low nit level and preferably a nit level no greater than about three.

Another object is to provide such an apparatus that comminutes one or more mats of non-crosslinked cellulose fibers which have been impregnated with a crosslinking substance, where the comminution is performed before the crosslinking substance is dried and cured.

Another object is to provide such an apparatus that minimizes the breakage of individual fibers.

Another object is to provide such an apparatus that yields crosslinked fibers having substantially no knots.

The foregoing objects and other features and advantages of the present invention will be more fully understood as the detailed description thereof proceeds, particularly when considered together with the accompanying drawing.

DETAILED DESCRIPTION

Overall System

Figure 1:
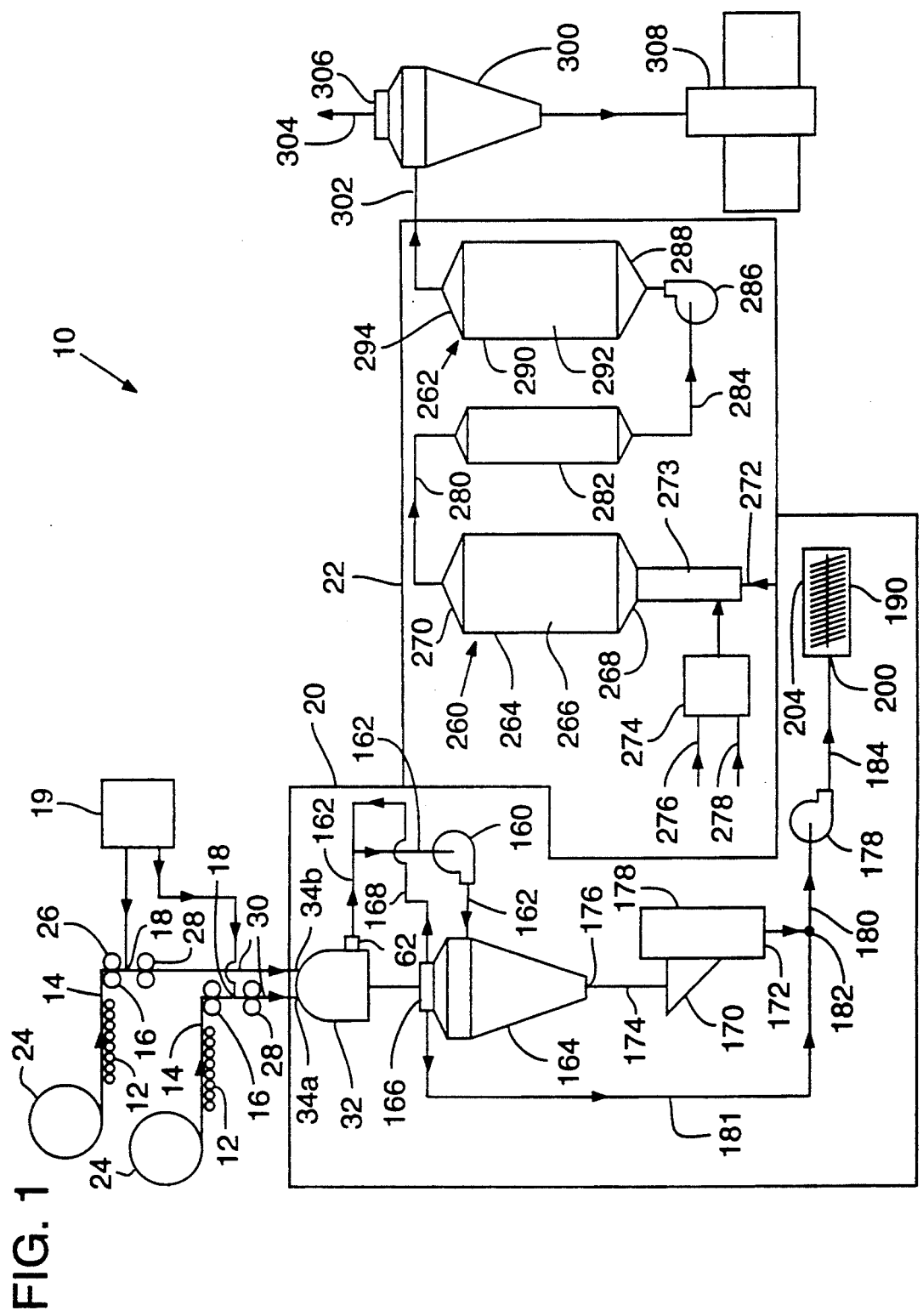
FIG. 1 is a schematic depiction of the components of the apparatus of the present invention.

The apparatus 10 (FIG. 1) of the present invention comprises a conveying device 12 for transporting a mat 14 of cellulose fibers or other fibers through a fiber treatment zone 16; an applicator 18 for applying a treatment substance such as a crosslinking substance from a source 19 thereof to the mat 14 at the fiber treatment zone 16; a novel type of fiberizer 20 for completely separating the individual cellulose fibers comprising the mat 14 to form a fiber output comprised of substantially unbroken cellulose fibers substantially without nits or knots; and a dryer 22 coupled to the fiberizer for flash-evaporating residual moisture from the fiber output and for curing the crosslinking substance, thereby forming dried and cured cellulose fibers. The apparatus 10 of the present invention has been observed to consistently produce fibers with a nit level of less than three, which is substantially lower than obtainable using any apparatus presently known in the art.

Raw Materials

As used herein, a "mat" denotes any non-woven sheetlike structure comprising cellulose fibers or other fibers that are not covalently bonded together. The fibers may be obtained from wood pulp or other source including cotton "rag", hemp, grasses, cane, husks, cornstalks, or any other suitable source of cellulose fiber that can be laid into a sheet.

Preferably, the mat 14 includes a debonding agent which can be applied after formation of the mat 14 or added to cellulose fibers before forming the mat therefrom. For example, with mats comprising pulp fibers, the debonding agent can be added to wet pulp before the mat is laid using conventional papermaking machinery. Debonding agents tend to minimize interfiber bonds between fibers of the mat. A fair, but nonexhaustive, sampling of debonding agent is disclosed in U.S. Pat. Nos. 3,395,708 and 3,544,862 to Hervey, et al.; U.S. Pat. No. 4,144,122 to Emanuelsson, et al.; U.S. Pat. No. 3,677,886 to Forssblad, et al; U.S. Pat. No. 4,351,699 to Osborne III; U.S. Pat. No. 4,476,323 to Hellsten, et al.; and U.S. Pat. No. 4,303,471 to Laursen, all of which are herein incorporated by reference. Any suitable debonding agents may be used, such as preferably Berocell 584 from Berol Chemicals, Incorporated of Metairie, La. in a 0.25% weight of debonder to weight of fiber. However, use of a debonding agent is not required for complete fiberization using the present apparatus.

The mat 14 of cellulose fibers is preferably in an extended sheet form stored in the form of a roll 24 until use. While the mat 14 can also be one of a number of baled sheets (not shown) of discrete size, rolls 24 are generally more economically adaptable to a continuous process. The cellulose fibers in the mat 14 should be in a non-woven configuration produced by a pulping process or the like, such is in a paper mill, and can be bleached or unbleached. The mat 14 can have any of a wide variety of basis weights. For simplicity, FIG. 1 shows a roll 24 as the source of each mat 14, but it is to be understood that the mat 14 can be supplied in any form amenable for storing sheet-like structures. Also, the mat may be obtained directly from the headbox of paper making equipment or otherwise formed in any suitable manner.

It is normally not necessary that the cellulose fibers comprising the mat 14 be completely dry. Since cellulose is a hydrophilic substance, molecules thereof will typically have a certain level of residual moisture, even after air drying. The level of residual moisture is generally 10% w/w or less, which is not detectable as "wetness".

FIG. 1 also shows that more than one supply, such as multiple rolls 24, of the mat 14 of cellulosic fibers can be simultaneously processed using the present invention. For simplicity, FIG. 1 shows two rolls 24 being processed, but it is to be understood that even more supplies of cellulosic fibers can be simultaneously processed, depending upon the capacity of the equipment, particularly the fiberizer 20. As discussed herein below, the preferred embodiment of the fiberizer 20 can fiberize up to six mats at one time.

At the fiber treatment zone 16, sprayers or other applicators 18 apply chemicals such as crosslinking agents to the mat. Typically chemicals are applied uniformly to both sides of the mat. The wetted mat passes between a pair of rollers 28 which assist in distributing the chemicals uniformly through the mat. Other applicators may also, of course, be used.

The crosslinking substance is a liquid solution of any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

Preferred types of crosslinking substances are selected from a group consisting of urea derivatives such as methylolated urea, methylolated cyclic ureas, methylolated lower alkyl substituted cyclic ureas, methylolated dihydroxy cyclic ureas, and mixtures thereof. A specifically preferred crosslinking substance would be dimethyloldihydroxyethylene urea (DMDHEU). In addition, crosslinking substances can be based on polycarboxylic acids. Crosslinking materials are known in the art, such as described in the previously mentioned Chung patent, U.S. Pat. No. 4,935,022 to Lash, et al., U.S. Pat. No. 4,889,595 to Herron, et al., U.S. Pat. No. 3,819,470 to Shaw, et al., U.S. Pat. No. 3,658,613 to Steijer, et al., U.S. Pat. No. 4,822,453 to Dean, et al., and U.S. Pat. No. 4,853,086 to Graef, et al., all of which are hereby incorporated herein by reference.

Suitable catalysts include acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used.

In FIG. 1,. the crosslinking substance applied to the mat 14 is obtained from a supply 19 thereof, such as a tank or analogous vessel. It is also possible for the supply 19 of crosslinking substance to be continuously produced on-line to prevent pre-cure of the crosslinking substance that may occur over time if it were stored in a large vessel. On-line production of the crosslinking substance is particularly advantageous when it contains a catalyst. Alternatively, for example, a batch of the crosslinking substance can be prepared fresh each day, so long as no significant deterioration of the solution will occur during the period in which the batch is consumed.

Crosslinked cellulose fibers are individual fibers each comprised of multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents". Suitable crosslinking agents are generally of the bifunctional type which create covalently bonded "bridges" between said neighboring hydroxyl groups.

Crosslinked cellulose fibers have particular applicability not only in wrinkle-resistant fabrics but also in materials derived from wood pulp having one or more desirable characteristics such as high loft, low density, high water absorbency, resiliency, and light weight. As a result, crosslinked cellulose fibers are candidates for use in absorbent structures found in disposable products such as diapers and pads. They are also useful for paper toweling, wiping cloths, filters, and other similar uses.

Despite their desirable qualities, crosslinked cellulose fibers have previously enjoyed limited success as a raw material. A principal reason for this is because the most convenient way for a manufacturer to crosslink cellulose fibers is by application of the crosslinking agent to a cellulosic fibrous sheet or mat which must be subsequently fiberized (all the constituent fibers of the sheet or mat separated from one another) before the fibers can be subjected to a step in which the crosslinking agent is cured. If any curing occurs before the fibers are completely separated, interfiber bonding can occur which would make any subsequent attempt at complete fiberization virtually impossible.

Crosslinked cellulose fibers when used in many products cannot have excessive amounts of certain defects known in the art as "knots" and "nits". Knots are agglomerations of fibers remaining after an incomplete fiberization of a cellulosic fibrous sheet. Nits may be defined as hard, dense agglomerations of fibers held together by the crosslinking substance due to the ability of crosslinking agents to covalently bond individual fibers together (interfiber bonding). Nits are generally regarded in the art as having a surface area of about 0.04 $mm^2$ to about 2.00 $mm^2$. A nit usually has a density greater than 0.8 $g/cm^3$, where a density of about 1.1 $g/cm^3$ is typical. The fibers comprising a nit virtually cannot be separated from one another in a conventional fiberizing device. As a result, these recalcitrant particles become incorporated into the final product where they can cause a substantial degradation of product aesthetic or functional quality. For example, nits can substantially reduce the absorbency, resiliency, and loft of an absorbent product. For aesthetically sensitive products, such as high quality paper, a "nit level" of three or less (two or fewer nits per 6-inch diameter test "handsheet"; see Example 1) is generally regarded as a maximally acceptable number of nits. Knots can also seriously degrade product appearance. Also, as an example of the effect of these particles on product performance, filters made using crosslinked fibers containing any nits and knots would in many cases be incapable of performing to specifications.

Conveying Device

Referring further to FIG. 1, each mat 14 of cellulosic fibers is conveyed by a conveying device 12, which can comprise, for example, a conveyor belt or a series of driven rollers with the mat positioned therebetween. The conveying device 12 carries the mats through the fiber treatment zone 16. FIG. 1 also shows a further portion of one type of conveying device comprised of a first pair of rollers 26 and a second pair of rollers 28 for each mat 14. The first and second pair of rollers 26,28 are particularly effective for urging the corresponding mat at a substantially constant and controlled rate of speed.

Fiber Treatment Zone

Each mat 14 is urged by the first and second pair of rollers 26, 28 through the fiber treatment zone 16 where the mat 14 is impregnated with a liquid crosslinking substance. The crosslinking substance is preferably applied to one or both surfaces of the mat using any of a variety of methods known in the art useful for such a purpose, such as spraying, rolling, dipping, or analogous method. Spraying has the advantage of consistent and rapid full coverage of a planar surface such as that of a mat at a controllable rate, especially when the spray is applied to a surface moving past a spray nozzle or analogous applicator at a fixed rate. Roller applicators have also proven to be reliable and effective in such applications as paper coating and the like and would therefore be effective for applying the crosslinking substance in the present instance. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

The rollers 28 can be positioned relative to each other to have a defined gap therebetween so as to enable them to impart a controlled squeeze action to the impregnated mat as it departs the fiber treatment zone 16. As mentioned above, such squeezing action facilitates complete and uniform penetration of the crosslinking substance throughout the thickness dimension of the mat. The squeezing action also helps to regulate the degree of saturation ("loading level") of the mat 14 with the crosslinking substance.

Fiberizer

The next subsystem following the fiber treatment zone is a fiberizer 20 which serves to comminute one or more mats 30 impregnated with the crosslinking substance into individual substantially unbroken cellulose fibers comprising a fiber output. The fiberizer 20 performs its task on one or more mats, which are preferably still moist (but which may be dry) from application of the crosslinking agent. In this case, the wet sheets are delivered directly and immediately to the fiberizer by the conveyor 12 without aging or other significant delays. As detailed below, the preferred embodiment of the fiberizer 20 is designed to minimize interfiber bonding and the formation of nits therein. Also, the preferred embodiment of the fiberizer 20 thoroughly fiberizes each impregnated mat 30, thereby virtually eliminating residual knots.

Figure 10:
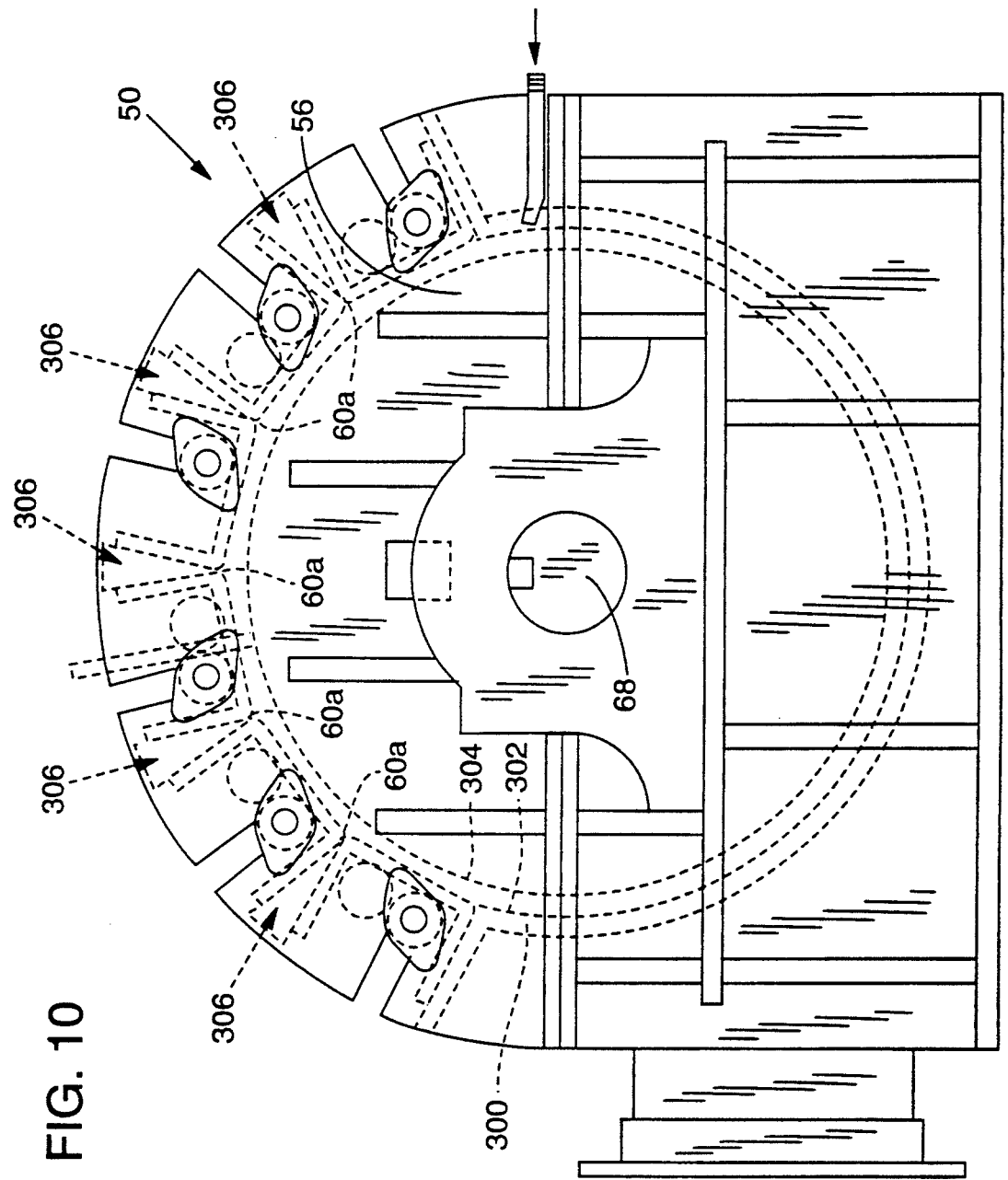
FIG. 10 is an end elevation view of the fiberizer of the present invention.

The preferred embodiment of the fiberizer 20 comprises an attrition device 32 as detailed hereinbelow and in copending U.S. patent application entitled "Fiberizing Apparatus" to Mark W. Bowns, et al., filed on Oct. 31, 1990, U.S. patent application Ser. No. 07/607,312, which is incorporated herein by reference. The attrition device 32 preferably can simultaneously fiberize a plurality of impregnated mats. As shown in FIG. 10, the lower main body of the housing 50 is formed by a wall 300 which forms the lower section of the housing. Feed mechanism supports described below form the upper portion of the housing. The wall 300 and feed mechanism supports in effect define a smooth closed cylindrical interior surface 302 (FIG. 10) of the housing. The housing may also be formed by simply extending the wall 300 such that the wall 300 is of circular cross-section and forms the entire housing body as a continuous, uninterrupted smooth cylindrical wall. The ends of the housing are closed by respective end panels or walls.

The housing 50 also includes at least one, and preferably a plurality of elongated mat inlet slots 60a extending in a direction generally parallel to the longitudinal axis of the housing. As fiber mats are delivered through the respective slots 60a to the interior of the housing 50, a rotating rotor (which rotates through an effective rotor surface 304) engages the leading edge of the mats and fiberizes the mats into individual fibers. The rotor is driven by a motor 68 coupled by a shaft extending through an opening in the end plate 56. The effective rotor surface 304 is the surface swept by hammers of a rotor as the rotor is rotated. The arrangement of the guides 306 for introducing the mats into the housing are described more fully in co-pending application Ser. No. 07/607,312 filed Oct. 31, 1990.

Figure 2:
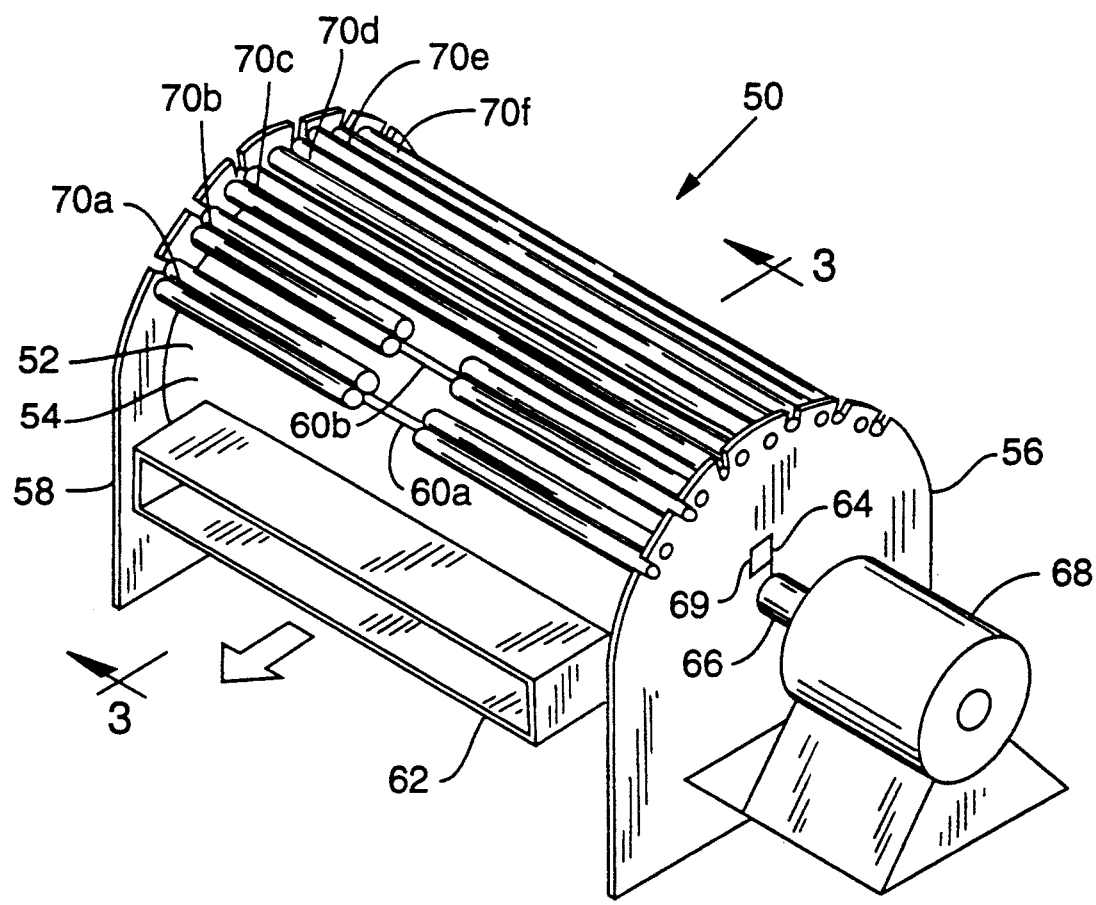
FIG. 2 is an isometric external view of a preferred embodiment of an attrition device, where certain details of the mat feeder assemblies have been omitted for clarity.

The exterior of a preferred embodiment of the attrition device 50 is shown in FIG. 2, which comprises an elongate cylinder-shaped housing 52 having an exterior surface 54. A first end panel 56 is located on one end of the housing 52 and a second end panel 58 is located at the other end of the housing 52. Multiple mat inlets (two of which 60a, 60b are shown) defined by the housing are located radially in an arc comprising a portion of the circumference of the housing 52, where each mat inlet is dedicated to feeding a separate mat into the attrition device 50. An outlet chute 62 extends from the housing 52. Each end panel 56, 58 defines a central orifice 64 through which coaxially extends a corresponding rotor shaft end 66 rotatable relative to the housing 52. One rotor shaft end 66 is coupled to a drive motor 68 serving to impart rotational motion thereto.

An air flow port 69 is provided through each end panel 56, 58. As a downstream blower 160 (discussed below) coupled to outlet 62 is operated, air is drawn in through openings 69, and around the ends of the rotor 100 (discussed below in connection with FIG. 4) to assist in minimizing the accumulations of fiber at such locations. Although variable, air typically flows at a rate of about 50 m$^3$/min through each of the openings 69. Also, a conduit (not shown) is typically included and coupled to wall 52 delivering water or other cleaning fluid to the interior of the housing through plural nozzle openings to clean any fiber accumulations from the attrition device. A liquid cleaning operation is typically accomplished by directing water toward the rotors in a direction somewhat counter to the direction of the normal rotor rotation as the rotor is rotated in this direction. Cleaning may be periodically performed, such as once every sixteen hours of operation of the attrition device, depending in part upon the volume of fiber being processed. By cleaning fiber accumulations in this manner, the accumulations do not end up in the finished product where they may comprise bonded nits.

Each mat inlet includes a feeder assembly, such as assemblies 70a-70f shown partially in FIG. 2, each mounted exteriorly relative to the cylindrical housing 52 at a location adjacent the corresponding mat inlet. A representative feeder assembly (such as 70d in FIG. 2) is shown in more detail in the transverse sectional view of FIG. 3. Each feeder assembly 70 is comprised of a first feed or seal roller 72 and a second feed or seal roller 74 extending longitudinally between the first and second end panels 56, 58 (FIG. 2). Also extending longitudinally between the first and second end panels 56, 58 are corresponding support angles or brackets (such as 76a and 76b in FIG. 3) and wedged shaped alignment or mounting bars (such as 78a and 78b in FIG. 3). Since FIG. 3 only depicts one feeder assembly 70d, angles 76a and 76b correspond to the feeder assembly 70d. The first and second seal rollers 72, 74 extend longitudinally in a direction substantially parallel to, and have a length substantially equal to the corresponding mat inlet 60a situated between a leg 80 of the angle bracket 76a and a leg 82 of the angle bracket 76b. The seal rollers 72, 74 are rotatably mounted for rotation about their respective longitudinal axes 84, 86 at locations equidistant from the mat inlet 60a. The distance D, from a plane through the axes of seal rollers 72, 74 to the effective rotor surface 144 swept by the hammers of the rotor 100 (FIG. 4) is preferably from about one-half inch to no more than about four inches when wet sheets are being fed to the rotor 100. This minimizes the possibility of plugging of the opening 60a as the sheets are being delivered thereto. In one specifically preferred design, each seal roller has a central shaft and an outer roll. The end of the central shaft of each seal roller 74 are coupled by a respective bearing to the end plates 56, 58. In addition, the ends of the central shaft of the seal rollers 72 are supported for rotation by a bracket (one being shown as 87 in FIG. 3). Typically the seal rollers are of a rigid material, such as steel, with the seal roller 74 being mounted at a fixed location. The ends of the shaft of the seal roller 72 are positioned within respective recesses 85 in the respective brackets 87. The bracket 87 may be pivotally coupled to the housing for pivoting in the direction of arrow 91 upon removal of a bolt or other stop 89. When bracket 87 is shifted upwardly in FIG. 3, the seal roller 72 may be removed for repair and or cleaning and to provide access to seal roller 74. Pneumatic cylinders, not shown, typically apply a load of from 5 psi to 80 psi to the respective ends of the shaft of the seal roller 72 to bias the seal rollers together. This pressure is typically relieved to allow the feeding of a sheet between the seal rollers and is then reinstated during normal operation of the attrition device. At least one of the seal rollers, such as roller 74, is rotatably driven via a motor (not shown) at a controlled angular velocity to advance a mat (not shown) situated between the first and second rollers 72, 74. Roller 74 may, for example, be driven in the direction of arrow 93 at a predetermined mat feed rate through the mat inlet 60a.

A first guide 88 and a second guide 90 are also mounted to the corresponding mounting brackets 76a and 76b, respectively. Each of the guides 88, 90 extend longitudinally in a direction substantially parallel to the corresponding seal rollers 72, 74, respectively. Each guide 88, 90 is typically constructed of a rigid material and includes an outer edge 92, 94, respectively, adjacent to, but spaced from the surface of the corresponding seal roller 72, 74, respectively, along the full length of the roller. The guides 88, 90 thereby serve to substantially prevent air from passing past the guides and to the corresponding mat inlet 60a. Therefore, substantially all of the air drawn into the attrition device passes through the openings 69 (as previously explained).

Figure 3:
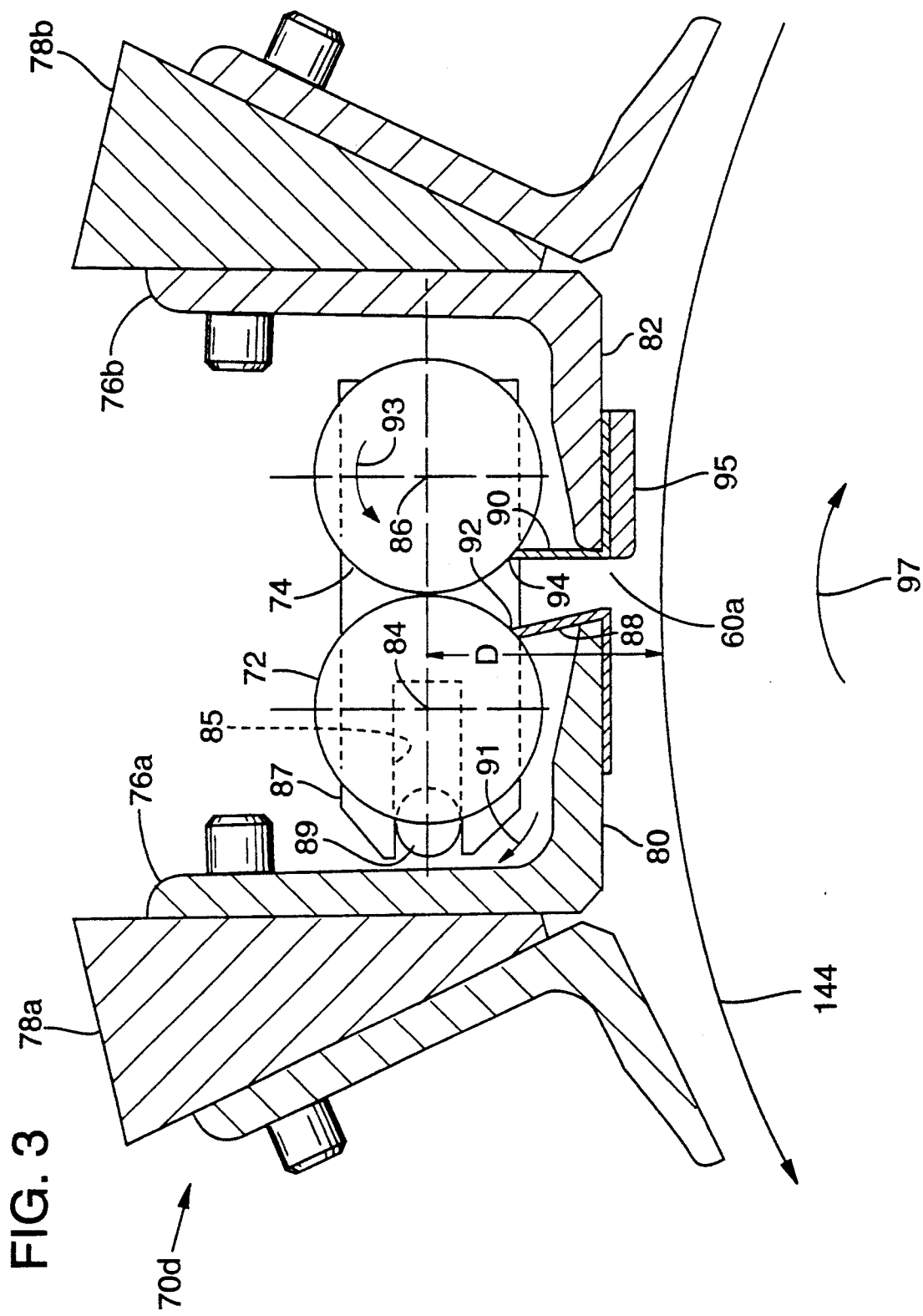
FIG. 3 is a transverse sectional view of a mat feeder assembly of the preferred embodiment of the attrition device.

The fiber mat passing through inlet 60a passes an optional nose bar 95 and is delivered against the rotor 100 traversing the effective rotor surface 144 (FIG. 3). The gap between the inlet 60a and the effective rotor surface is typically no more than about one-fourth to one inch.

Figure 4:
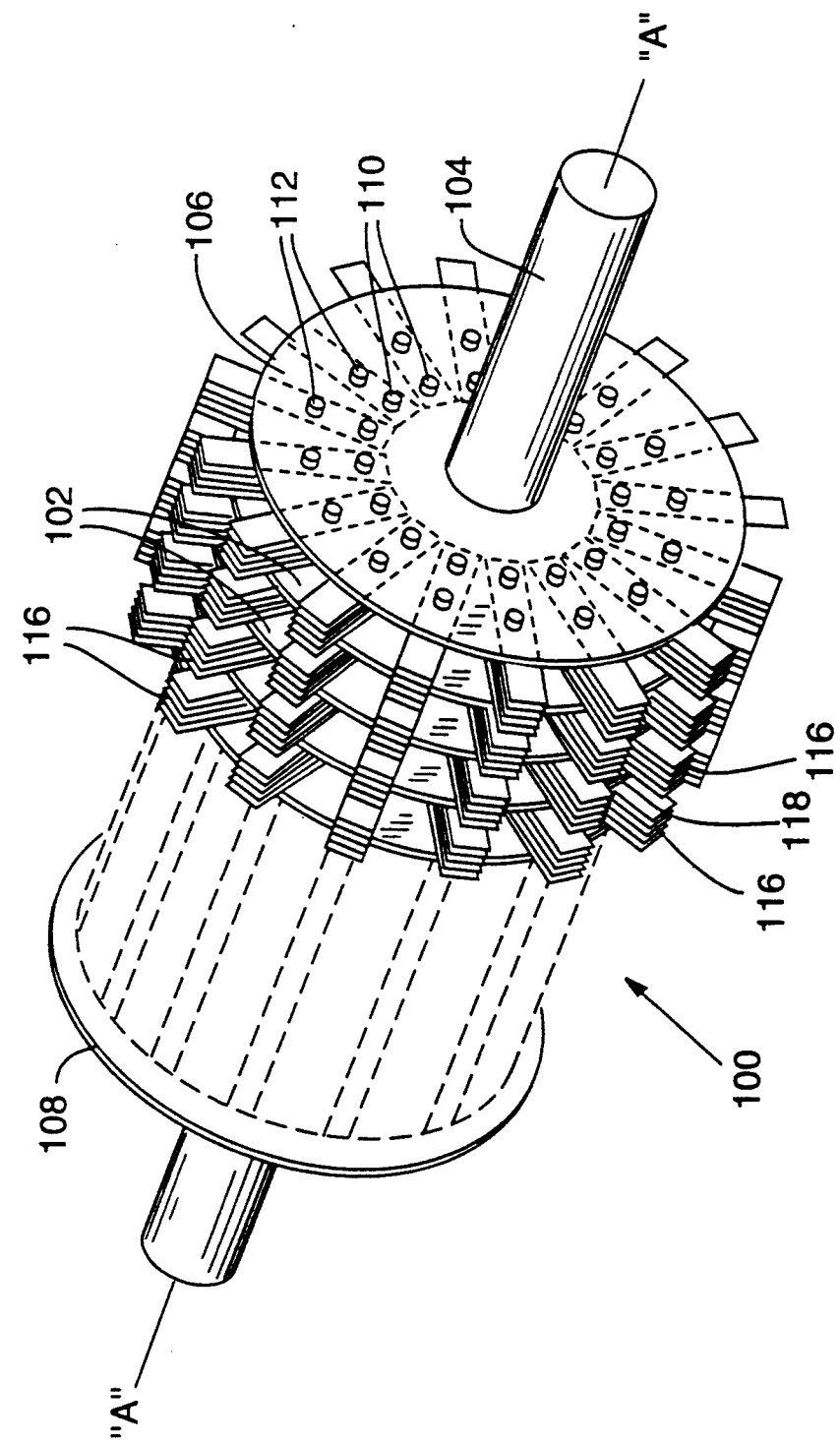
FIG. 4 is an isometric view of the rotor of the attrition device of FIG. 2.

FIG. 4 shows a rotor 100 of the type coaxially mounted inside the attrition device housing 52 (FIG. 1). The rotor 100 comprises a plurality of substantially annular spacer or hammer mounting plates 102 mounted to the rotor shaft 104. The plates 102 extend radially outwardly from the longitudinal axis "A" of the rotor shaft 104 and are parallel to one another. The rotor 100 also has a first rotor end plate 106 and a second rotor end plate 108, each substantially annular in shape and oriented parallel to the mounting plates 102. The first and second rotor end plates 106, 108 are mounted coaxially to the rotor shaft 104 and have a diameter sufficiently large such that only a narrow gap (e.g. one-sixteenth to one-half inch) is left between the inner surface of the cylindrical housing (not shown in FIG. 4) and the perimeter of the first and second end plates 106, 108. The illustrated plates 106, 108 extend radially outwardly beyond the distal ends of hammers 116 to minimize the possible accumulation of fibers adjacent to the end plates.

Attached to and extending between the first and second end plates are plural inner mounting rods 110 and an identical number of outer mounting rods 112 oriented parallel to the longitudinal axis "A" of the rotor shaft 104. The inner and outer mounting rods 110, 112 are secured to the first and second rotor end plates 106, 108. As shown clearly in FIG. 4, the mounting rods 110, 112 are arranged as plural equiangularly spaced pairs. Each pair comprises a single inner mounting rod 110 and a radially outwardly positioned single outer mounting rod 112. A typical rotor 100 has sixteen such pairs of rods arranged radially about the rotor axis "A".

Each pair of mounting rods 110, 112 has mounted thereto plural groups of hammer plates, each group comprising a hammer assembly 116. Each such hammer assembly 116 is located either between adjacent mounting plates 102 or between a spacing plate 102 and an adjacent rotor end plate 106, 108. However, each hammer assembly 116 is spaced from an adjacent hammer assembly 116, by an empty space 118 large enough to accommodate another hammer assembly. As a result, on a rotor 100 with twenty-seven mounting plates 102 and two rotor end plates 106, 108, for example, the maximal number of hammer assemblies 116 held by a given pair of mounting rods 110, 112 is fourteen.

Figure 5:
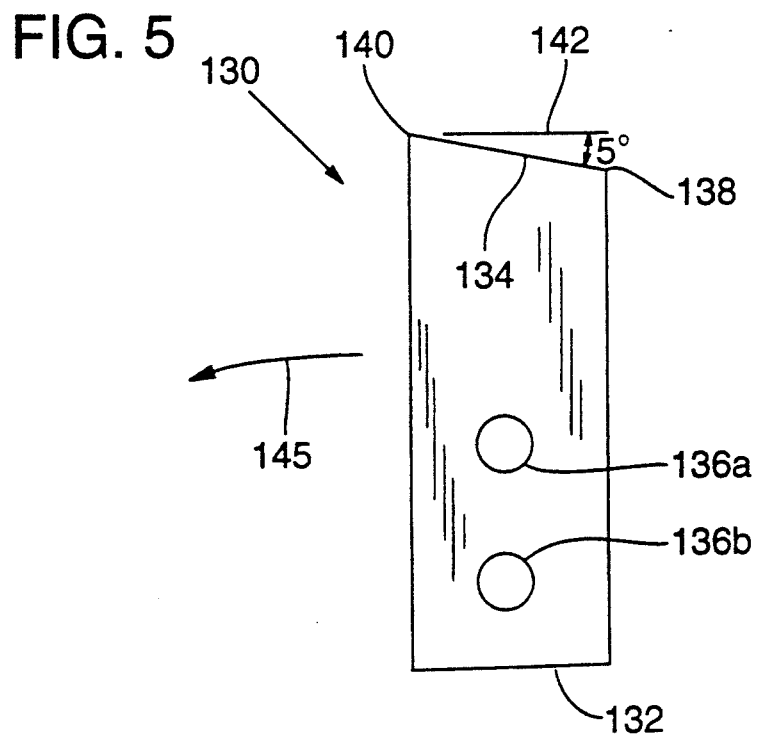
FIG. 5 is a plan view of a hammer plate used in the rotor of FIG. 4.

A representative flat hammer plate 130 of assembly 116 is depicted in FIG. 5, wherein each hammer plate 130 has a proximal end 132 positioned toward the rotor axis (not shown) and a distal end 134 positioned radially outward relative to the rotor axis. The hammer plate 130 also defines two mounting holes 136a, 136b for attaching the hammer 130 to an associated pair of mounting rods 110, 112 (not shown in FIG. 5). The distal end surface 134 of the hammer plate has a trailing edge 138 and a leading edge 140, wherein the leading edge 140 extends radially outward relative to the rotor axis beyond the trailing edge 138. The distal end 134 is cut at a five degree angle relative to a line 142 parallel to the proximal edge 132. The direction of rotation of the rotor is indicated by an arrow 145 in FIG. 5.

Figure 6:
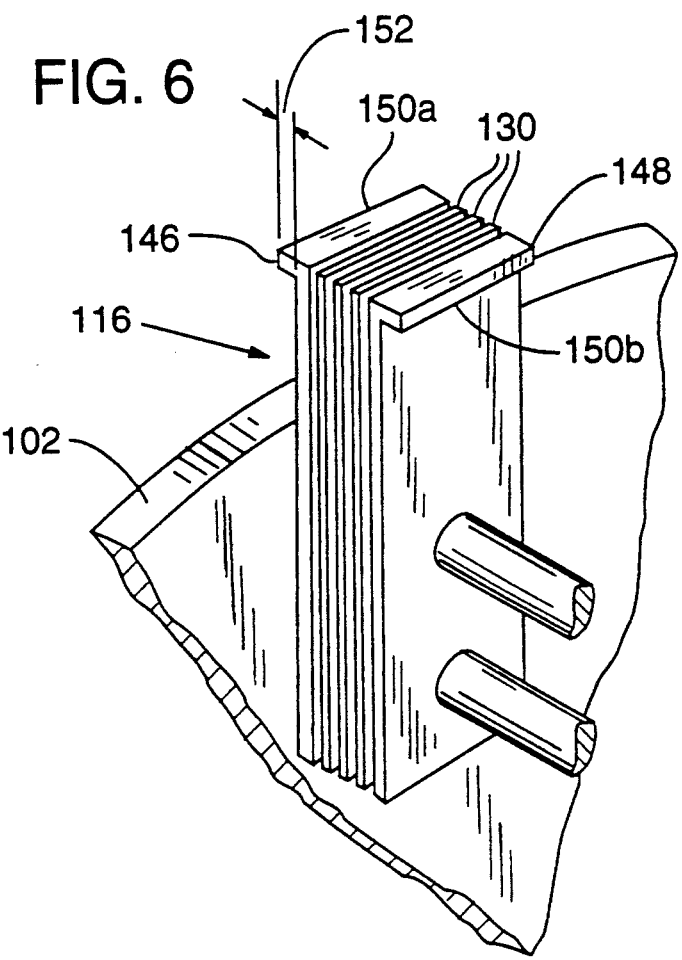
FIG. 6 is an isometric view of a stack of hammer plates used in the rotor of FIG. 4.

As shown in FIG. 6, each illustrated hammer assembly 116 comprises plural planar plate-like hammers 130 (three being shown in this figure). These plates are typically spaced apart by spacers (not shown). Each of said hammer assemblies 116 located between adjacent mounting plates 102 (only one plate 102 being shown in this figures) also includes a left-angled hammer 146 and a right-angled hammer 148 each having a lip 150a, 150b, respectively, extending transversely in an opposing direction relative to each other. The width dimension 152 of the lip of each angled hammer is typically equal to or slightly less than half the thickness dimension of a mounting plate 102. Also, each of the hammer assemblies 116 located between a plate 102 and a rotor end plate replaces one of the L-shaped hammers with a flat hammer plate adjacent to the end plate. Other hammer configurations and arrangements may be used. However, a preferred hammer arrangement minimizes any gaps in the surface swept by hammer elements to preferably no more than one-fourth of an inch.

The illustrated embodiment 50 of the attrition device is operated by driving the rotor 100 at a high angular velocity while feeding one or more impregnated mats through one more corresponding mat inputs. The mat is urged at a controlled linear velocity into the corresponding mat input slot 60 by the controlled rotation of the feed rollers 72, 74. As the impregnated mat enters a mat inlet, it is repeatedly impacted by the distal end surface and in particular, the leading edge of the hammer plates, which effectively and completely comminutes the mat into its individual constituent fibers, substantially free of knots and nits.

The preferred embodiment 50 of the attrition device as described hereinabove is particularly effective in simultaneously fiberizing one or more separate mats (up to six) to form a volume of individualized cellulose fibers having a nit level substantially lower than levels achievable with existing attrition devices such as hammermills. This is believed to be due to the fact that the present attrition device lacks hot spots and dead spaces, wherein fibers can accumulate, found in conventional hammermills or other attrition devices currently used in the art.

Referring further to FIG. 1, a first conveyer fan 160 of conventional design can be utilized for propelling the fibers from the outlet 62 of the attrition device 32 through a conduit 162.

An optional component of the fiberizer 20 is a first cyclone 164 or similar apparatus known in the art, utilized in a conventional manner to concentrate the fibers passing out of the outlet 62 of the attrition device 32. The first cyclone 164 receives the fibers through the conduit 162 coupled thereto.

Excess air can be recovered at the top 166 of the first cyclone 164 and recycled as required through a conduit 168 to a location upstream of the first conveyer fan 160 (if used). Such additional air can be beneficial for easing the transfer of the fibers through the first conveyor fan 160.

A disk refiner 168 is another optional component of the fiberizer 20 which can be employed to effect additional separation of fibers (removal of knots) if required. The disk refiner 168 is of a type known in the art and comprises a disk refiner inlet 170 and a disk refiner outlet 172. A representative disk refiner 168 is type DM36 manufactured by Sprout-Bauer, Incorporated of Muncie, Pa. If the disk refiner 168 is used, the inlet 170 thereof is coupled via a conduit 174 to an outlet 176 of the first cyclone 164.

A second conveyor fan 178 may optionally be utilized to urge propagation of the fibers through a conduit 180 downstream of the disk refiner 168. Excess air can be recovered from the top 166 of the first cyclone 164 and routed via a conduit 181 to a tee 182 just upstream of the second conveyor fan 178.

Another optional component of the fiberizer 20 is a fluff generator 190 which receives the fibers from the optional second conveyor fan 178 through a conduit 184. The fluff generator is described in detail below and in copending U.S. patent application entitled "Multi Pin Rotor Fiber Fluff Generator" to Mark W. Bowns, et al., filed on Oct. 31, 1990, incorporated herein by reference.

Figure 7:
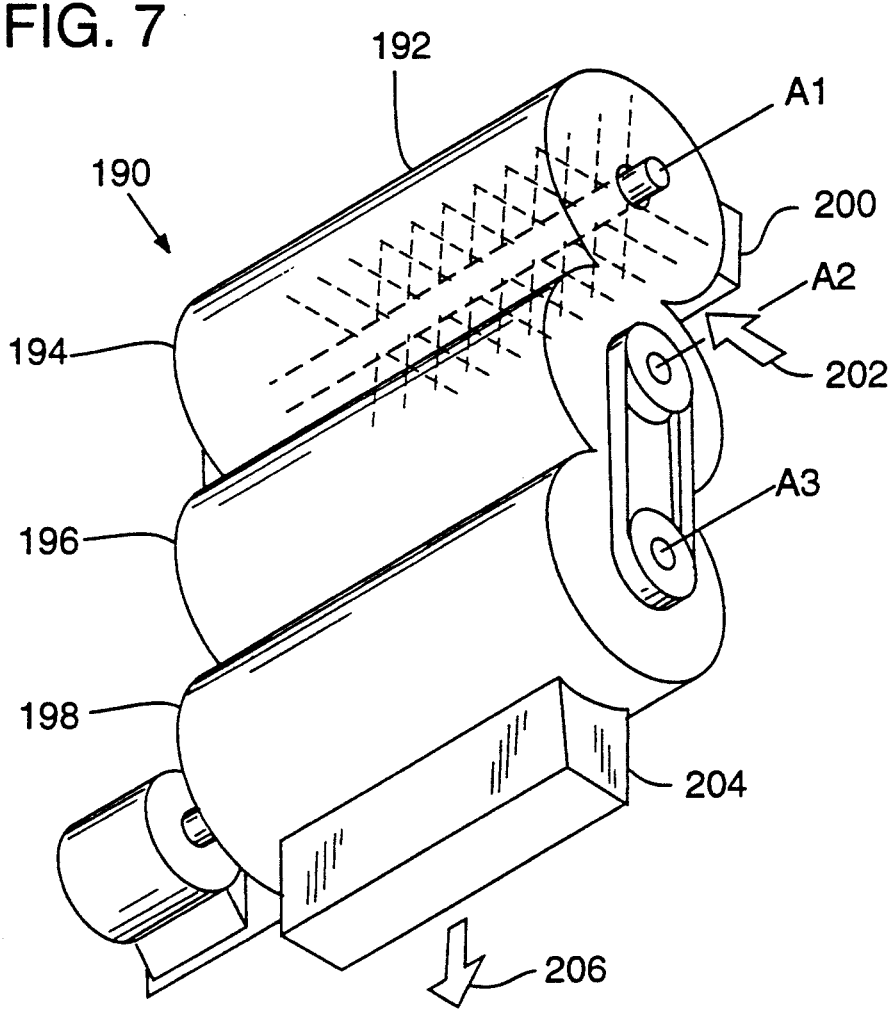
FIG. 7 is an isometric view of the exterior of a preferred embodiment of a fluff generator included as an option in the apparatus of the present invention.

Referring now to FIG. 7, a preferred embodiment of the fluff generator 190 comprises a housing 192 shaped in the form of three contiguous, partially intersecting cylinders, including a first housing portion 194 opening into a second (or middle) housing portion 196, which opens into a third housing portion 198. Each housing portion 194, 196, 198 has a longitudinal coplanar axis A1, A2, A3, respectively. The housing 192 has an inlet 200 permitting delivery (arrow 202) of fibers to the first housing portion 194, and an outlet 204 conducting fluffed fibers away (arrow 206) from the third housing portion 198.

Figure 8:
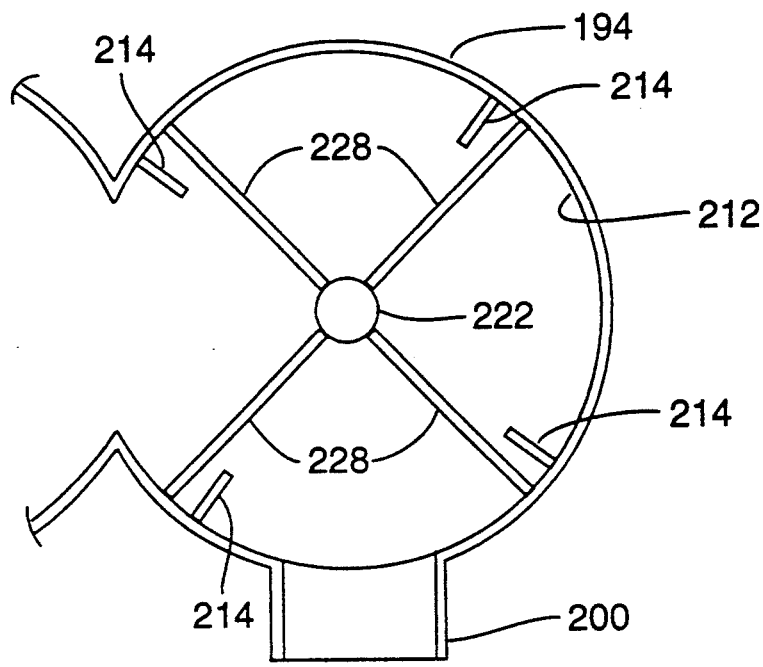
FIG. 8 is a transverse sectional view through a housing portion and rotor of the fluff generator of FIG. 7.

As shown in FIG. 8, showing a transverse sectional view of the first housing portion 194, the interior surfaces 212 of each of the first, second, and third housing portions have affixed thereto multiple stator pins 214 radially pointing toward the respective axis of the housing portion. The pins 214 are grouped in longitudinally extended rows along lines parallel to the respective housing portion axis.

Figure 9:
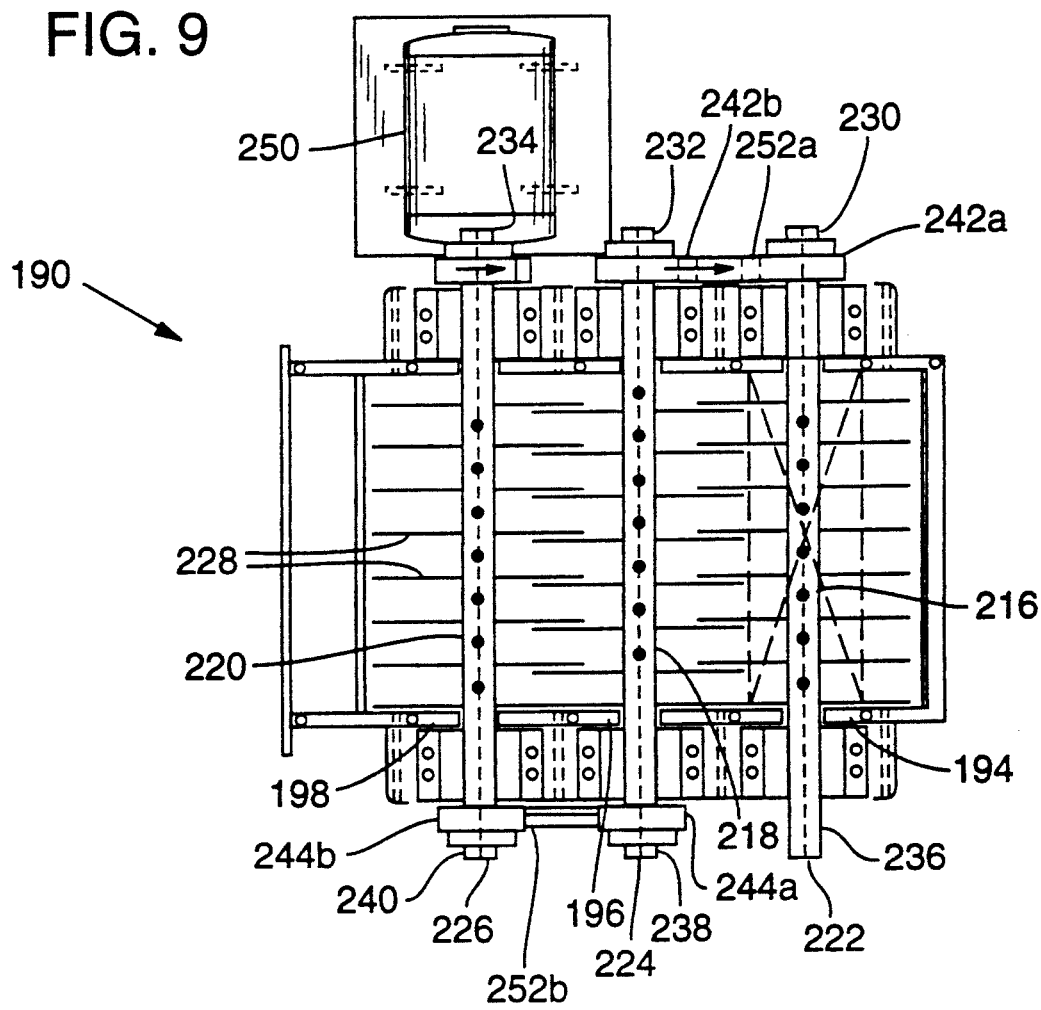
FIG. 9 is a plan sectional view of the fluff generator of FIG. 7.

Each of the first, second, and third housing portions 194, 196, 198, respectively, is in surrounding relationship to a first rotor 216, a second rotor 218, and a third rotor 220, respectively, as shown in FIG. 9. Each rotor 216, 218, 220 has a corresponding rotor shaft 222, 224, 226 coaxial with the axis A1, A2, A3 of the respective housing portion. As shown in FIG. 8 (showing a transverse sectional view of the first housing portion 194 only, but applicable to illustrate similar details inside the second housing portion 196 and third housing portion 198) and FIG. 9, to the shaft 222 of the rotor 216 are mounted four longitudinally extended rows of plural rotor pins 228, where each row of rotor pins 228 is equiangularly spaced in a radial manner around the corresponding rotor shaft 222. The rotor pins 228 radially extend from the shaft 222 nearly to the inside surface 212 of the corresponding housing portion 194 but are positioned on the rotor shaft 222 such that they will pass between longitudinally adjacent stator pins 214 when the rotor 216 is rotating about its axis. Rotor shafts 224 and 226 are similarly equipped with rotor pins 228.

As shown in FIG. 9, each rotor shaft 222, 224, 226 has a first end 230, 232, 234, respectively, and a second end, 236, 238, 240, respectively, each extending through and journaled in the corresponding housing portion 194, 196, 198, respectively. The first and second ends of each rotor shaft extend outside the corresponding housing portion. A pulley 242a, 242b is attached to each of the first ends 230, 232, respectively, of the first and second rotor shafts 222, 224, respectively. Likewise, a pulley 244a, 244b is attached to the second ends 238, 240, respectively, of the second and third rotor shafts 224, 226, respectively. The first end 234 of the third rotor shaft is rotatably coupled directly or indirectly to a drive motor 250. Each set of pulleys is coupled by a drive belt 252a, 252b ensuring that, when the drive motor 250 rotates the third rotor 220, the second and first rotors 218, 216, respectively, synchronously rotate in the same rotational direction as the third rotor 220.

The fluff generator 190 is operated by synchronously driving the rotors 216, 218, 220 at a high rotational speed and conducting fibers 202 (FIG. 7) from the disk refiner 168 (FIG. 1), where the velocity of said fibers is increased via the second conveyor fan 178, into the inlet 200 of the fluff generator 190. The fibers are conducted sequentially through the first, second, and third housing portions 194, 196, 198, respectively and exit 206 the fluff generator 190 through the outlet 204. As the fibers pass through the housing 192 of the fluff generator 190, they encounter strong agitation and turbulence generated by the groups of rotor pins 228 on each of the three rapidly rotating rotors 216, 218, 220 passing by the stationary stator pins 214. By encountering such turbulence and agitation, any knots remaining in the fibers are comminuted to form a fiber output containing virtually no knots.

As used herein, the "fiber output" is the mass of thoroughly individualized fibers exiting the fiberizer 20 and passing to the dryer 22.

As discussed hereinabove, the disk refiner 168 and fluff generator 190 are optional components of the present apparatus 10. In most cases, the attrition device 32 alone is adequate for completely fiberizing plural mats. However, in cases where the mats are unusually bulky, the disk refiner 168 and fluff generator 190 can be employed, particularly to ensure the absence of knots in the fiber output.

Dryer

Referring further to FIG. 1, a preferred embodiment of the present apparatus 10 includes a dryer 22 which is utilized to perform two sequential functions: remove residual moisture from the fibers and cure the crosslinking agent. Preferably, the dryer 22 comprises a drying zone 273 for receiving fibers, e.g. from fluff generator outlet 204 and for removing residual moisture from the fibers via a "flash drying" method and a second drying zone 260, 262 for curing the crosslinking agent. In FIG. 1, the curing starts in zone 260 and continues through zone 262.

The FIG. 1 embodiment shows that zone 273 is coupled to the fluff generator outlet by a conduit 272 and to a source 274 of heated air, typically produced by combustion of a supply of natural gas 276 and fresh air 278. The temperature of heated air is regulated to maintain the temperature of the drying zone 273 within a range of about 200° C. to about 315° C. As the fiber output passes into the drying zone 273, the wet fibers comprising the fiber output are substantially instantaneously exposed to the high temperature in this zone. Such rapid exposure to high temperature imparts a "flash drying" effect to the fibers, thereby causing rapid and thorough drying. Such "flash drying" also tends to separate, in a microscopically explosive manner, fibers that are touching one another, thereby ensuring thorough separation of the fibers. The passage time through the drying zone 273 is preferably less than one second, which is deliberately kept short to avoid overheating and scorching the fibers, which become highly susceptible to scorching after the residual moisture has been driven therefrom.

The FIG. 1 embodiment shows that the first zone 260 is comprised of a first tower 264 comprised of a body portion 266, an inlet 268, and a first tower outlet 270. The dryer zone 273 is coupled via a conduit 272 to the outlet of the fluff generator 190. Since the fluff generator 190 is an optional component, it is also possible to couple the dryer zone 273 directly to the outlet 62 of the attrition device 32 if neither the fluff generator 190 nor the disk refiner 168 are included.

In FIG. 1, the first tower outlet 270 is shown preferably coupled via a conduit 280 to a down tube 282, which is coupled via a conduit 284 to a third conveyor fan 186 located at an inlet 288 of a second tower 290.

The third conveyor fan 286 performs the function of transporting the fibers through the dryer which thereby pass through the inlet 288 of the second tower 290.

The second tower 290 is shown which includes the inlet 288, a second tower body 292, and an outlet 294 serving as an outlet of the dryer 22. Dried fibers are propelled through the inlet 288 of the second tower 290 via the third conveyor fan 286. As the fibers are lofted through the second tower body 292, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as to not scorch the fibers during curing. It should be noted that single stage dryers may also be used.

The dried and cured fibers exiting the dryer outlet 294 have an extremely low level of nits and virtually no knots. Further, they are not discolored from scorching and the like, and have a median fiber length substantially unchanged from the median length of the fibers comprising the mat 14.

FIG. 1 also shows a second cyclone 300 of conventional design coupled via a conduit 302 to the dryer outlet 294, serving to concentrate the fibers passing therethrough in preparation for collection. Excess air 304 is vented through the top 306 of the second cyclone 300. The resulting concentrated fibers can be collected using any of a number of collection devices 308 known in the art, such as fiber bagging devices.

EXAMPLE I

In this example, non-woven fibrous mats were impregnated with a crosslinking agent, fiberized, dried, and cured using the apparatus as diagrammed schematically in FIG. 1.

Two 52-inch wide mats of southern pine kraft wood pulp fibers (type NB316 from Weyerhaeuser Company) and having a basis weight of 680 g/m$^2$ were fed to apparatus. The mats were impregnated using dimethyloldihydroxyethylene urea at a concentration of about 5%, applied over both sides of each mat using a combination of spray nozzles and impregnation rollers. The loading level of crosslinking agent was about 4.5% w/w.

The treated fiber mats were fed at the rate of 8 meters/min. to the attrition device 32. The specific attrition device used in this example was equipped with six mat inlets and a rotor having 16 rows of hammers as described above around the circumference of the rotor. The rotor had a diameter of 30 inches and was rotated at an angular velocity of 1200 rpm by an electric motor. Other rpm rates have also been tested and have proven satisfactory, including extremely high rpm rates.

Random samples of fibers were obtained from the output attrition device and observed for nits. These samples were 2.6 grams and were consistently observed to have fewer than three nits on the average with most samples having no nits. The attrition device was flushed with water once every sixteen hours for cleaning purposes.

A disk refiner was employed downstream of the attrition device. This specific disk refiner was a DM36 refiner as previously mentioned.

A fluff generator as described in FIGS. 7-9 was also employed in this downstream of the disk refiner.

The temperature at the dryer input in this example was within the range of 200° C. to 315° C. The temperature at the second tower outlet was within the range of 140° C. to 180° C.

Crosslinked fiber at the output of the dryer was produced at a rate of about 5000 pounds per hour and had a nit level on an average of from 1 to 3 and a maximum bulk of greater than 22. Bulk and nit levels were determined by the following procedure, involving the production of test "handsheets" with a diameter of about 6 inches:

A "British handsheet mold" was filled with 3 to 4 inches of water. To approximately 750 mL of water were added 1.2 grams of pulp, available from Weyerhaeuser Company, followed by agitation using a Waring blender for 20 seconds to yield a pulp slurry. A 2.4 gram sample of the above obtained crosslinked fiber was added to the pulp slurry in the blender followed by agitation therein for another 10 seconds. The resulting slurry was added to the handsheet mold up to a fill mark. The slurry in the mold was gently mixed using a spatula for 3 seconds, then drained, leaving the pulp wet laid on the screen in the mold. The wet pulp layer was blotted to remove as much moisture as possible, then removed from the screen. The resulting handsheet was dried between two blotters on a drum dryer, then weighed to the nearest 0.01 gram immediately after drying.

Bulk was determined using a caliper, performed immediately after drying. Mean thickness was determined using five thickness determinations of various locations on the handsheet. Bulk was calculated in units of cm³/g as follows:

$$\frac{\text{(mean thickness) cm } (20.38) \text{ cm}^2}{\text{(Handsheet weight) grams}} = \text{Bulk}$$

Nit level was determined by examination of the handsheet and simple determination of the number of nits present on the handsheet. If no nits were observed, a nit level of 1 was assigned to the test sheet; if 1 nit was observed, a nit level of 2 was assigned to the sheet; if 2 nits were observed, a nit level of 3 was assigned to the sheet; and so forth for higher nit levels.

Therefore, the apparatus of the present invention effectively produces a low nit level product, and one of high bulk even when crosslinking agents are used.

Having illustrated and described the principles of the present invention in a preferred embodiment and variations thereof, it should be apparent to those skilled in the art that the invention can be modified in arrangement and detail without departing from such principles. We claim all modifications coming within the spirit and scope of the following claims.

We claim:

1. A method of producing crosslinked cellulose fibers, comprising:
    applying a crosslinking substance to a mat of cellulose fibers at a fiber treatment zone;
    conveying the mat directly from the fiber treatment zone to a fiberizer without pausing for curing;
    fiberizing the mat in the fiberizer by separating the cellulose fibers of the mat into a fiber output of substantially unbroken individual cellulose fibers with a nit level of no more than about three by fiberizing the mat in a fiberizer comprising a housing with a rotor mounted therein that includes a plurality of hammers projecting outwardly from the rotor, each hammer having a distal end which in cooperation with the distal ends of the other hammers forms a surface of rotation when the rotor is rotated, the surface of rotation having individual gaps no more than about one-fourth inch wide that are not swept by the distal ends of the hammers, the housing having an inner cylindrical surface that is no more than about one-fourth to one inch from the surface of rotation, the inner cylindrical surface being smooth so as to substantially lack internal hot spots and dead spaces that would promote formation of nits, thereby minimizing heating, crosslinking, and formation of nits in the fiberizer; and
    drying and curing the fiber output to form dried and cured fibers.

2. The method of claim 1 wherein the hammers are longitudinally and circumferentially spaced on the rotor such that each hammer is longitudinally and circumferentially adjacent an empty space large enough to accept the hammer.

3. The method of claim 2 wherein the hammers are aligned in longitudinal rows.

4. The method of claim 1 wherein the step of applying a crosslinking substance comprises applying a polycarboxylic acid to the mat at the fiber treatment zone.

5. The method of claim 1 wherein each flat distal hammer end comprises a surface extending transversely away from a body of the hammer.

6. The method of claim 5 wherein the hammers are longitudinally and circumferentially spaced on the rotor such that each hammer is longitudinally and circumferentially adjacent an empty space large enough to accept the hammer.

7. The method of claim 1 wherein the rotor has end walls, and the method further comprises the step of introducing a flow of air into the housing adjacent the end walls to move fiber away from the end walls.

8. A method of producing crosslinked cellulose fibers, comprising the steps of:
    applying a polycarboxylic acid crosslinking substance to a mat of cellulose fibers at a fiber treatment zone;
    conveying the mat directly from the fiber treatment zone to a fiberizer without pausing for curing;
    fiberizing the mat in a fiberizer by separating the cellulose fibers on the mat into a fiber output of substantially unbroken individual cellulose fibers with a nit level of no more than about three by fiberizing the mat in a fiberizer comprising a housing with a rotor mounted therein that includes a plurality of hammers projecting outwardly from the rotor, each hammer having a flat distal end which in cooperation with the distal ends of the other hammers forms a surface of rotation when the rotor is rotated, wherein the surface has individual gaps of no more than one-fourth inch that are not swept by the distal ends of the hammers, the hammers being aligned in longitudinal rows with the hammers longitudinally and circumferentially spaced on the rotor such that each hammer is longitudinally and circumferentially adjacent an empty space large enough to accept the hammer, the fiberizer housing having a smooth inner cylindrical surface which substantially lacks hot spots and dead spaces, the surface being no more than about one-fourth to one inch from the surface of rotation, each flat distal hammer end comprising a surface extending transversely away from a body of the hammer; and drying and curing the fiber output to form dried and cured fibers.

* * * * *

UNITED STATES PATENT AND TRADEMARK OFFICE
CERTIFICATE OF CORRECTION

PATENT NO. : 5,324,391
DATED : June 28, 1994
INVENTOR(S) : Allan R. Carney, Peter A. Graef, Mark W. Bowns, Clifford R. Bolstad, Fred E. Olmstead and Frank R. Hunter It is certified that error appears in the above-identified patent and that said Letters Patent is hereby corrected as shown below:

Title page, [75] Inventors, include --Frank R. Hunter, Bellevue--.

Signed and Sealed this

Nineteenth Day of January, 1999

Attest:

Attesting Officer

*Acting Commissioner of Patents and Trademarks*